United States Patent
Sharonov

(10) Patent No.: US 9,592,109 B2
(45) Date of Patent: Mar. 14, 2017

(54) HERNIA MESH PLACEMENT SYSTEM AND METHOD FOR IN-SITU SURGICAL APPLICATIONS

(71) Applicant: Covidien LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 424 days.

(21) Appl. No.: 14/164,596

(22) Filed: Jan. 27, 2014

(65) Prior Publication Data
US 2014/0276996 A1 Sep. 18, 2014

Related U.S. Application Data
(60) Provisional application No. 61/776,808, filed on Mar. 12, 2013.

(51) Int. Cl.
*A61B 90/13* (2016.01)
*A61F 2/00* (2006.01)

(52) U.S. Cl.
CPC ............ *A61F 2/0063* (2013.01); *A61B 90/13* (2016.02)

(58) Field of Classification Search
CPC ....... A61B 90/13; A61B 90/10; A61F 2/0063; A61F 2002/0068; A61F 2002/0072
See application file for complete search history.

(56) References Cited

U.S. PATENT DOCUMENTS

| | | | |
|---|---|---|---|
| 5,383,477 A | 1/1995 | DeMatteis | |
| 5,598,269 A * | 1/1997 | Kitaevich | A61B 6/08 356/399 |
| 5,807,387 A | 9/1998 | Druais | |
| 6,267,502 B1 | 7/2001 | McNeirney et al. | |
| 6,597,941 B2 | 7/2003 | Fontenot et al. | |
| 6,946,666 B2 | 9/2005 | Saito et al. | |
| 7,281,849 B2 | 10/2007 | Sohal et al. | |
| 2002/0087047 A1* | 7/2002 | Remijan | A61B 1/00142 600/109 |
| 2004/0092970 A1 | 5/2004 | Xavier | |
| 2007/0055291 A1 | 3/2007 | Birkmeyer et al. | |
| 2008/0039715 A1 | 2/2008 | Wilson et al. | |
| 2008/0051632 A1* | 2/2008 | Ito | A61B 1/0607 600/114 |
| 2008/0051636 A1 | 2/2008 | Murayama | |
| 2009/0216253 A1* | 8/2009 | Bell | A61F 2/0045 606/153 |
| 2010/0106194 A1 | 4/2010 | Bonutti et al. | |

* cited by examiner

*Primary Examiner* — Tuan V Nguyen
*Assistant Examiner* — Chima Igboko

(57) ABSTRACT

A method for hernia mesh placement during in-situ surgical applications. The method includes the step of positioning a mesh having a center mark within an abdominal cavity near a site of repair. A light assembly projecting a light beam through a free end is provided. Next, the free end of the light assembly is inserted through a central location of the site of repair. Finally, the center mark of the mesh is aligned with the light beam of the light assembly to position the mesh at the central location of the site of repair.

15 Claims, 4 Drawing Sheets

HERNIA MESH PLACEMENT SYSTEM AND METHOD FOR IN-SITU SURGICAL APPLICATIONS

CROSS-REFERENCE TO RELATED APPLICATIONS

This application claims the benefit of and priority to U.S. Provisional Patent Application No. 61/776,808, filed Mar. 12, 2013, the entire disclosure of which is incorporated by reference herein.

BACKGROUND

1. Technical Field

The present disclosure relates to a system and method for aligning a hernia mesh with a central location of a hernia defect. More particularly, the present disclosure provides a light assembly inserted into the center of a hernia defect configured to emit a light beam and a hernia mesh with a marking. The marking is aligned with the light beam to align the mesh with the hernia defect.

2. Background of Related Art

Minimally invasive surgery to treat surgical hernias are desirable in that they allow for quicker recovery time and shorter hospital stays as compared to open surgical procedures. Minimally-invasive procedures also leave minimal scarring (both internally and externally) and reduce patient discomfort during the recovery period.

Surgical hernias are abnormal protrusions of an organ or other body structure through a defect or natural opening in a covering membrane, e.g., a wall of a cavity that normally contains the organ or other body structure. For example, inguinal hernias are, typically, caused by soft tissue from the intestines protruding through the inguinal wall. Ventral hernias, on the other hand, are caused by internal organs pushing through to a weak spot in the abdominal wall.

The use of prosthetic mesh has now become accepted practice in the treatment of patients with both inguinal and ventral hernias, as well as other types of hernias, e.g., hiatal, femoral, umbilical, diaphragmatic, etc. To endoscopically apply the mesh for hernia repair, a surgical region (i.e., adjacent the cavity wall) is, typically, insufflated using a biocompatible fluid (e.g., $CO_2$). Subsequently, a surgeon selects points on the cavity wall where the surgeon believes the mesh will be affixed.

In certain instances, prior to affixing the mesh, the mesh is, initially, held in position by pressing on the mesh from outside the body while observing the mesh through a laparoscope or, conversely, pressing upward against the mesh with the use of one or more suitable devices, e.g., an atraumatic grasper or the like. Thereafter, the surgical mesh is often affixed, e.g., sutured or tacked using a fastener, to the cavity wall by conventional techniques.

Unfortunately, this method has shortcomings. Once the mesh is initially held in position, a surgeon cannot view the exact location for optimal placement of the mesh along the abdominal wall. Accordingly, a need exists for a system and method that allows the surgeon to clearly see the location of the hernia so that the hernia repair mesh is properly placed along the abdominal wall to treat a patient.

SUMMARY

In an embodiment of the present disclosure, a method for hernia mesh placement during in-situ surgical applications is provided. The method includes the steps of positioning a mesh having a center mark within an abdominal cavity near a site of repair. A light assembly projecting a light beam through a free end is also provided. The method is continued by inserting the free end of the light assembly through a central location of the site of repair. Finally, the center mark of the mesh is aligned with the light beam of the light assembly to position the mesh at the central location of the site of repair. The method further includes positioning the mesh by disposing the mesh between an endoscope and the site of repair within an abdominal wall.

In one embodiment, the light assembly includes a body and a hollow shaft extending therefrom. The hollow shaft permits the light beam from the body therethrough. The free end of the shaft defines a needle-shaped configuration to facilitate penetration through tissue. Preferably, the light beam is a laser beam.

The method further includes the step of mounting the light assembly to a support assembly exterior of the abdominal cavity after inserting the free end of the hollow shaft.

In another embodiment, a method for hernia mesh placement during in-situ surgical applications is discussed. The steps include identifying a site of repair along an abdominal wall of an abdominal cavity of a patient. Next, a mesh having a center mark within the abdominal cavity is positioned between an endoscope and the site of repair. A light assembly configured to project a light beam through a free end is also provided. The method further includes inserting the free end of the light assembly through a central location of the site of repair and activating the light beam. Next, the location of the light beam from within the abdominal cavity is viewed through the endoscope. Finally, the center mark of the mesh is aligned with the light beam and the mesh is attached to the abdominal wall.

In yet another embodiment a method for hernia mesh placement during in-situ surgical applications is disclosed. The steps include positioning a mesh within an abdominal cavity near a site of repair. Next, a plurality of light assemblies emitting a light beam through a free end is provided. The free ends are inserted near the site of repair at predetermined locations corresponding to the shape and size of the mesh. The mesh is then aligned with the light beams to place the mesh near the site of repair.

In one embodiment, each light assembly includes a shaft with a free end defining a needle-shaped configuration to facilitate penetration through tissue. The free end has a light-emitting diode configured to illuminate the abdominal cavity.

In an alternate embodiment, each light assembly includes a shaft with a free end defining a needle shaped configuration to facilitate penetration through tissue. The free end has optical fibers in communication with a light-emitting diode disposed at an opposing end. The optical fibers are configured to illuminate the abdominal cavity.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
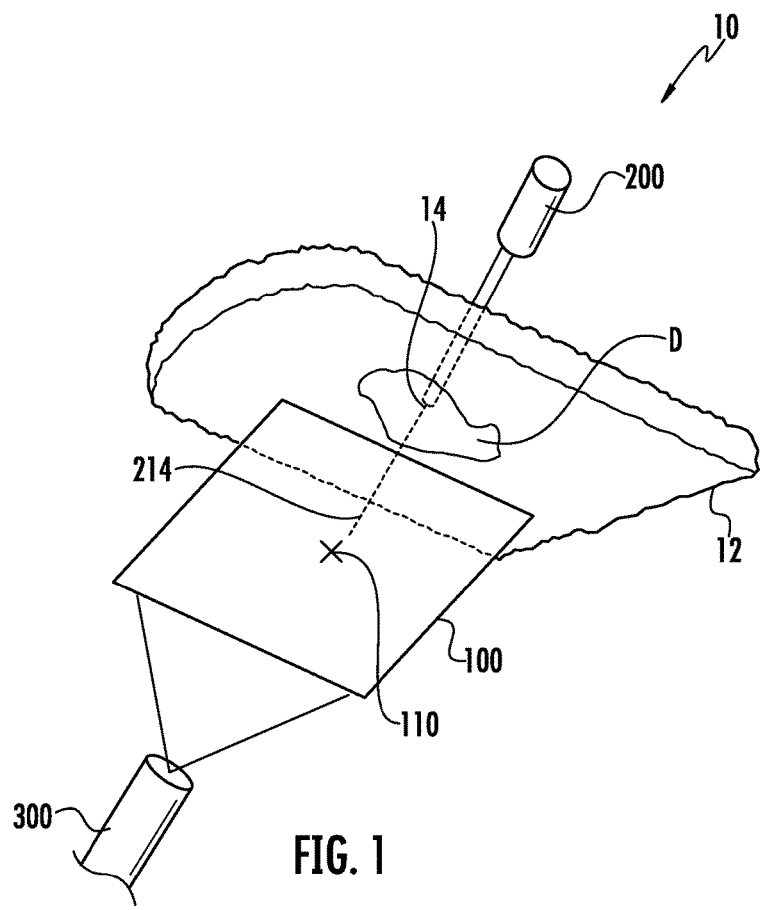
FIG. 1 is a perspective view of a system according to an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail. Although the present disclosure is discussed in terms of a minimally invasive endoscopic procedure, the presently disclosed instrument is usable in other minimally invasive procedures.

During endoscopic procedures, it is often difficult to position nontransparent materials such as hernia repair mesh on a site of repair. At the final stage of placement, the mesh is in between an endoscope and the site of repair. Correct placement of the mesh along the abdominal wall of a patient becomes difficult as the repair site is no longer in a site of view.

Referring to FIG. 1, there is disclosed a system 10 for use in minimally invasive surgery. The system 10 is configured to assist in correct placement of hernia repair mesh 100 over a site of repair, such as a hernia defect "D", generally, along the abdominal wall 12 of a patient. The system 10 includes a light assembly 200, a hernia repair mesh 100, and an endoscope 300.

Figure 2:
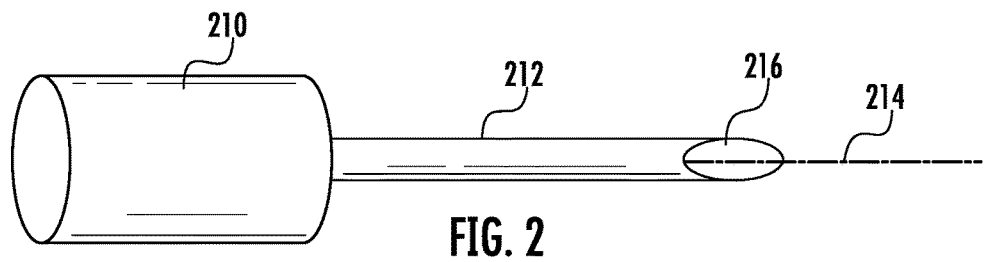
FIG. 2 is a side view of a light assembly of the system according to an embodiment of the present disclosure.

The light assembly 200 (as shown in FIG. 2) serves as an optical guidance for mesh placement. In one embodiment, the light assembly 200 consists of a body 210 having a hollow shaft 212 extending therefrom. The body 210 is configured to emit a light beam 214. The hollow shaft 212 permits the light beam 214 from the body 210 therethrough such that the light beam 214 can be viewed from a free end 216 of the hollow shaft 212. Preferably, the light beam 214 is a laser beam with very high light intensity that is visible through bodily tissue. The free end 216 of the hollow shaft 212 defines a needle-shaped configuration to facilitate penetration through tissue of the abdominal wall 12. The hollow shaft 212 is inserted through the hernia defect "D" by use of the free end 216 puncturing the tissue. In an alternate embodiment, a trocar or cannula (not shown), such as those well known in the art, is used to provide entry for the hollow shaft into the abdominal cavity. While light assembly 200 is depicted in a central portion of defect D, it may be located at an offset from the defect. The offset may be at a known distance and angular relationship to the defect.

Figure 3:
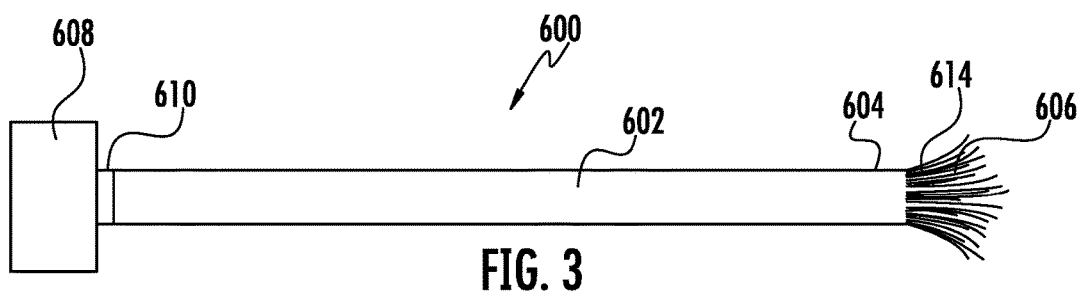
FIGS. 3 and 4 are side views of alternate embodiments of light assemblies according to the present disclosure.
Figure 4:
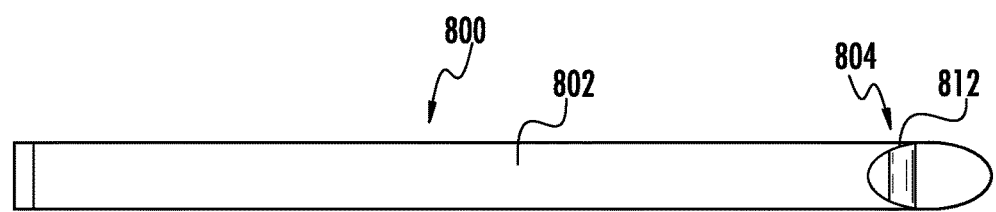

FIG. 3 shows an alternate embodiment of optical guidance for use with the present disclosure. A light beacon 600 is shown having a shaft 602 having a free end 604 defining a needle shaped configuration 614 to facilitate penetration through tissue. The free end 604 of the shaft has optical fibers 606 in communication with a light source, preferably a light-emitting diode (LED), 608 disposed at an opposing end 610. The light source provides enough light for visualization of the mesh at a few centimeters distance. FIG. 4 illustrates yet another alternate embodiment of a light beacon 800 having a small light source 812 disposed within the shaft 802 near the free end 804, which includes wiring for LED power.

With continued reference to FIG. 1, the mesh 100 is shown within the abdominal cavity. The mesh 100 described herein may include porous fabrics made from intertwined filaments. The filaments may be monofilaments or multi-filaments and, in embodiments, a plurality of multi-filaments may be combined to form yarns. The filaments may extend horizontally and vertically in a manner which produces sections where the filaments cross-over one another creating points of common intersection. The mesh 100 may be woven, non-woven, knitted or braided. In some embodiments, the filaments may form two-dimensional or three-dimensional meshes. As shown in FIG. 1, the mesh 100 includes a center mark 110 highlighting the midpoint "M" of the mesh 100. Although the mesh 100 is shown as rectangular in shape in FIG. 1, it is understood than any suitable shape and size may be used as per the size of the hernia defect "D".

The endoscope 300 as shown in FIG. 1 is of a typical type well known in the art. The endoscope 300 is inserted into the patient through a natural opening near the abdominal cavity. The endoscope 300 has a light and video imaging (now shown) capability that is used to aide the surgeon when looking inside the abdominal cavity.

Still referring to FIG. 1, the method of placing the mesh in the center of the hernia defect "D" will now be described. First, the surgeon identifies a site of repair caused by a hernia defect "D" along the abdominal wall 12 of a patient. The measurement of the hernia defect "D" may be carried out manually by the surgeon by means known in the art. After the location for attaching the mesh 100 has been determined, the surgeon marks the center of the mesh 100 with an "X" or similar identifier with known techniques and materials. Alternatively, the mesh 100 may have a predetermined indicia already dispersed thereon. The surgeon then positions the mesh 100 having the center mark 110 within the abdominal cavity between the endoscope 300 and the hernia defect "D". The mesh 100 being inserted into the abdominal cavity by means well known in the art.

Next, the surgeon readies the light assembly 200. The surgeon can maneuver the light assembly 200 by grasping the body 210. The surgeon inserts the free end 216 of the hollow shaft 212 through the midpoint "M" of the identified hernia defect "D" using the needle shaped configuration to penetrate tissue of the abdominal wall 12. At this point, the surgeon may utilize a support assembly 400 (shown in FIG. 6) to maintain the positioning of the light assembly 200 exterior of the abdominal cavity. This allows the light beam 214 to be locked into position during the remainder of the procedure. The support assembly 400 generally includes a support base 410 and one or more support arms 420. The support arm 420 includes hinges or joints 425 to facilitate manipulating the support to a desired configuration for retaining the light assembly 200 in a desired position. After inserting the free end 216, the light beam 214 is activated to illuminate the midpoint "M" of the hernia defect "D". As discussed, the light beam 214 is preferably a laser beam which is visible within the abdominal cavity and from behind the mesh 100.

Using the endoscope 300 to view the location of the light beam 214, the surgeon then aligns the center mark 110 of the mesh 100 with the light beam 214. As a result, the mesh 100 is aligned at the midpoint "M" along the hernia defect "D". Finally, the surgeon affixes the mesh 100 to the abdominal wall 12 via tacking, suturing or other well known methods in the art.

Figure 5:
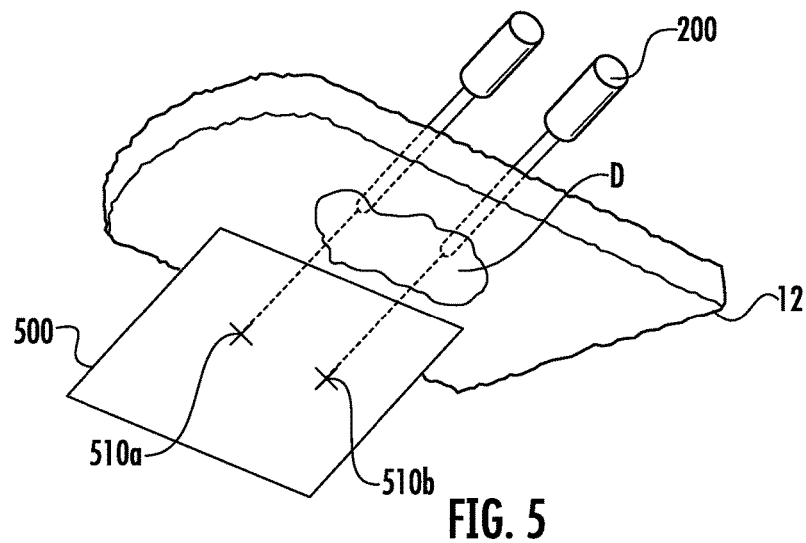
FIG. 5 is perspective view of a plurality of a light assemblies used in accordance with an alternate embodiment of the present disclosure.

The method disclosed hereinabove relates to a single mesh aligned with a central location of a hernia defect "D". However, for additionally accuracy in aligning the mesh with the hernia defect "D", the surgeon may choose to use at least two light assemblies to illuminate the location of the defect "D". In this embodiment as shown in FIG. 5, when the surgeon measures the hernia defect "D", the surgeon determines at least two locations "L1" and "L2" for inserting at least two light assemblies 200. Accordingly, the mesh 600 is marked with corresponding markers 510a, 510b to match locations "L1" and "L2" within the hernia defect "D". Using a similar method as described above, the surgeon inserts the free ends 216 of the at least two light assemblies 200 through the abdominal wall 12. To position the mesh 600, the surgeon aligns the at least two light beams 214 with the at least two marks 610a, 610b on the mesh 600. In alternate embodiment, the surgeon may choose to mark each corner of the mesh. Using a plurality light assemblies and a mesh with each corner marked appropriately, the surgeon then aligns each corner with a respective light beam.

Figure 6:
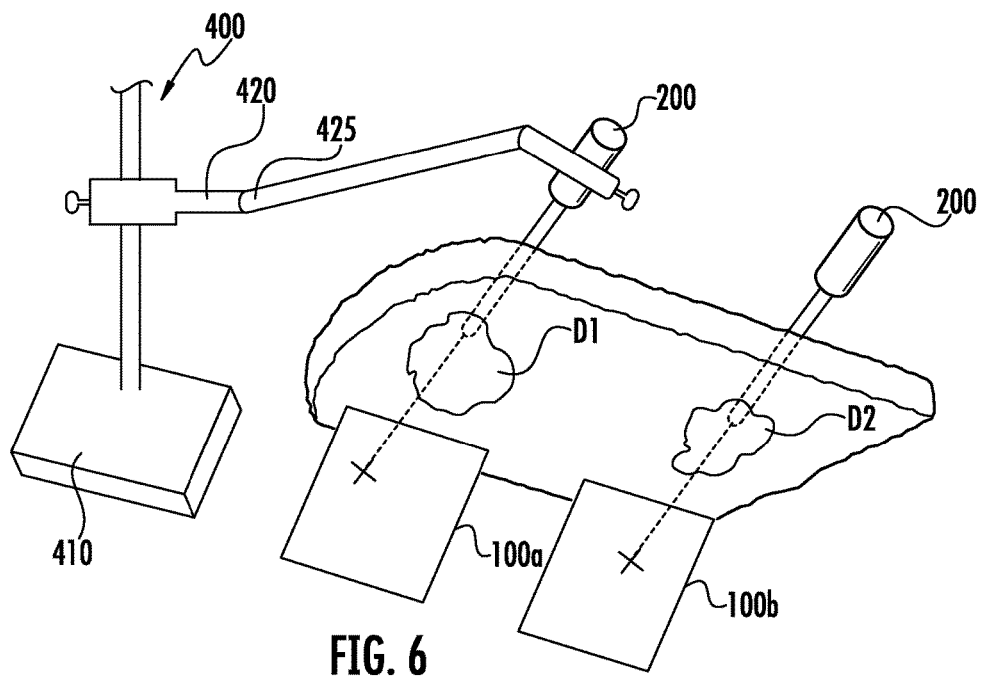
FIG. 6 is a perspective view of a plurality of light assemblies and plurality of mesh materials used in accordance with another alternate embodiment of the present disclosure.

Based on the size and location of the hernia defect "D", the surgeon may determine that more than one mesh is required. Alternatively, the surgeon may also identify several hernia defects "D" and require more than one mesh 100 be placed along the abdominal wall 200 of the patient. FIG. 6 illustrates an embodiment wherein multiple hernia defects "D1" and "D2" located along the abdominal wall 200 of the patient each require placement of a mesh 100a, 100b in accordance with the method described herein.

Figure 7:
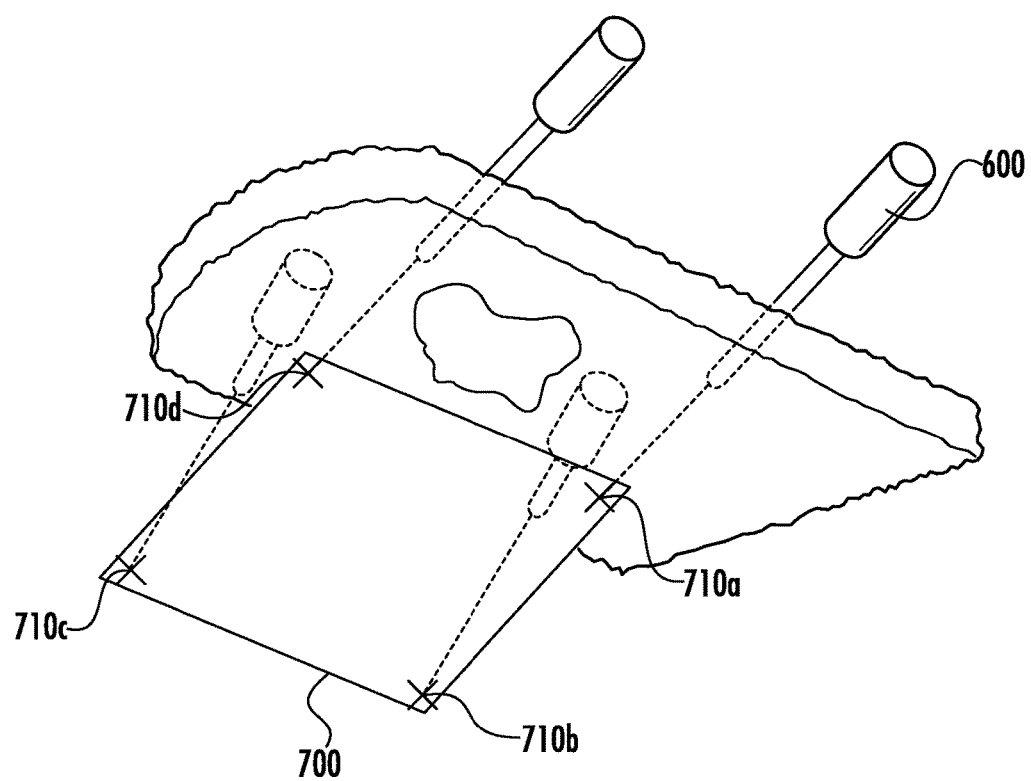
FIG. 7 is perspective view of a plurality of light assemblies used in accordance with yet another embodiment of the present disclosure.

In other instances the surgeon may find the hernia defect "D" is too thin to puncture the middle of the defect "D" safely with the light assembly. In this instance, the surgeon may mark the mesh 700 at the corners 710a, 710b, 710c, 710d and use a plurality of light assemblies to align the corners of the mesh 700 surrounding the defect "D". As shown in FIG. 7, a plurality of light beacons 500 are used to highlight around the hernia defect "D" and thus surgeon may match each corner of the mesh 700 with each light beacon 500 to cover the defect "D".

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for hernia mesh placement during in-situ surgical applications, the method comprising:
   positioning a mesh having a center mark on a first surface of the mesh within an abdominal cavity near a site of repair;
   projecting a light beam through a free end of a light assembly;
   inserting the free end of the light assembly through a central location of the site of repair;
   illuminating a second surface of the mesh opposite the first surface with the light beam of the light assembly; and
   aligning the center mark of the mesh with the light beam of the light assembly to position the mesh at the central location of the site of repair.

2. The method according to claim 1, wherein positioning the mesh includes disposing the mesh between an endoscope and the site of repair within an abdominal wall.

3. The method according to claim 2, wherein projecting the light beam includes the light assembly having a body and a hollow shaft extending therefrom, the hollow shaft permitting the light beam from the body therethrough, wherein the hollow shaft includes the free end of the light assembly which defines a needle-shaped configuration to facilitate penetration through tissue.

4. The method according to claim 3, wherein projecting the light beam includes the light beam being a laser beam.

5. The method according to claim 4, further including mounting the light assembly to a support assembly exterior of the abdominal cavity after inserting the free end of the hollow shaft.

6. A method for hernia mesh placement during in-situ surgical applications, the method comprising:
   identifying a site of repair along an abdominal wall of an abdominal cavity of a patient;
   positioning a mesh having a center mark on a first surface of the mesh within the abdominal cavity between an endoscope and the site of repair with the first surface facing the endoscope and a second surface, opposite the first surface facing the site of repair;
   inserting a free end of a light assembly through a central location of the site of repair;
   activating a light beam to project through the free end of the light assembly to illuminate the second surface of the mesh;
   viewing the location of the light beam from within the abdominal cavity through the endoscope;
   aligning the center mark of the mesh with the light beam; and
   attaching the mesh to the abdominal wall.

7. The method according to claim 6, wherein inserting the free end of the light assembly includes the light assembly having a body and a hollow shaft extending therefrom, the hollow shaft permitting the light beam from the body therethrough, wherein the hollow shaft includes the free end of the light assembly which defines a needle-shaped configuration to facilitate penetration through tissue.

8. The method according to claim 7, wherein activating the light beam includes the light beam being a laser beam.

9. The method according to claim 8, further including mounting the light assembly to a support assembly exterior of the abdominal cavity after inserting the free end of the light assembly.

10. A method for hernia mesh placement during in-situ surgical applications, the method comprising:
    positioning a mesh within an abdominal cavity near a site of repair, the mesh being rectangular and including markings at each of four corners of the mesh:
    emitting a light beam through a free end of each light assembly of a plurality of light assemblies;
    inserting the free ends of four light assemblies of the plurality of light assemblies near the site of repair at predetermined locations corresponding to the four corners of the mesh; and
    aligning the mesh with the light beams.

11. The method according to claim 10, wherein positioning the mesh within an abdominal cavity near a site of repair includes disposing the mesh between an endoscope and the site of repair within an abdominal wall.

12. The method according to claim 10, wherein inserting the free ends of four light assemblies includes each of the four light assemblies having a shaft including the free end of the light assembly which defines a needle-shaped configuration to facilitate penetration through tissue, each free end of the four light assemblies having a light-emitting diode therein configured to illuminate the abdominal cavity.

13. The method according to claim 12, wherein inserting the free ends of the four light assemblies includes at least one free end having optical fibers in communication with the light-emitting diode configured to illuminate the abdominal cavity.

14. The method according to claim 12, further including mounting at least one light assembly of the plurality of light assemblies to a support member exterior of the abdominal cavity after inserting the free end of the at least one light assembly.

15. The method according to claim 10, wherein aligning the mesh with the light beams includes matching the markings of the mesh to the corresponding light beams to align the mesh with the site of repair.

* * * * *